US010567658B2

United States Patent
Inose et al.

(10) Patent No.: US 10,567,658 B2
(45) Date of Patent: Feb. 18, 2020

(54) IMAGE PROCESSING DEVICE, IMAGE PROCESSING METHOD, IMAGE PROCESSING PROGRAM

(71) Applicant: OLYMPUS CORPORATION, Hachioji-shi, Tokyo (JP)

(72) Inventors: Kenji Inose, Saitama (JP); Naoyuki Akiyama, Kanagawa (JP)

(73) Assignee: OLYMPUS CORPORATION, Tokyo (JP)

(*) Notice: Subject to any disclaimer, the term of this patent is extended or adjusted under 35 U.S.C. 154(b) by 9 days.

(21) Appl. No.: 16/045,395

(22) Filed: Jul. 25, 2018

(65) Prior Publication Data
US 2018/0332227 A1 Nov. 15, 2018

Related U.S. Application Data

(63) Continuation of application No. PCT/JP2016/059971, filed on Mar. 28, 2016.

(51) Int. Cl.
*H04N 5/232* (2006.01)
*A61B 1/04* (2006.01)
(Continued)

(52) U.S. Cl.
CPC .......... *H04N 5/23267* (2013.01); *A61B 1/04* (2013.01); *G06T 7/0002* (2013.01); *H04N 9/07* (2013.01)

(58) Field of Classification Search
None
See application file for complete search history.

(56) References Cited

U.S. PATENT DOCUMENTS

| 6,049,354 A * | 4/2000 | Sekine | H04N 5/23267 348/207.99 |
| 2006/0061658 A1* | 3/2006 | Faulkner | H04N 5/23254 348/207.1 |

(Continued)

FOREIGN PATENT DOCUMENTS

| JP | H06253191 A | 9/1994 |
| JP | 2004329514 A | 11/2004 |

(Continued)

OTHER PUBLICATIONS

International Search Report (ISR) dated May 17, 2016 issued in International Application No. PCT/JP2016/059971.

(Continued)

*Primary Examiner* — Quan Pham
(74) *Attorney, Agent, or Firm* — Holtz, Holtz & Volek PC

(57) ABSTRACT

An image processing device includes: a movement-amount calculating unit that calculates a movement amount of an object image between a latest frame and a past frame in the same color channel; a shake-correction-amount calculating unit that calculates a shake correction amount for the latest frame on the basis of the movement amount; a stable-shake-correction-amount calculating unit that calculates a stable shake-correction amount for the latest frame; a shake correcting unit that performs shake correction processing on the latest frame on the basis of the stable shake-correction amount; and a storage unit that stores the stable shake-correction amount, wherein the stable-shake-correction-amount calculating unit calculates the stable shake-correction amount for the latest frame on the basis of the shake correction amount for the latest frame and a stable shake-correction amount for a frame in a different color channel from the latest frame, stored in the storage unit.

6 Claims, 12 Drawing Sheets

(51) Int. Cl.
*H04N 9/07* (2006.01)
*G06T 7/00* (2017.01)

(56) References Cited

U.S. PATENT DOCUMENTS

| | | |
|---|---|---|
| 2006/0274156 A1 | 12/2006 | Rabbani et al. |
| 2012/0120216 A1 | 5/2012 | Morita |
| 2012/0262559 A1 | 10/2012 | On |
| 2013/0165753 A1 | 6/2013 | Takahashi |

FOREIGN PATENT DOCUMENTS

| | | |
|---|---|---|
| JP | 3660731 B2 | 6/2005 |
| JP | 2006149483 A | 6/2006 |
| JP | 2007243335 A | 9/2007 |
| JP | 2008541662 A | 11/2008 |
| JP | 2010041416 A | 2/2010 |
| JP | 2012055498 A | 3/2012 |
| JP | 2012217579 A | 11/2012 |
| JP | 2013258468 A | 12/2013 |
| JP | 5562808 B2 | 7/2014 |
| WO | 2006124237 A2 | 11/2006 |

OTHER PUBLICATIONS

Written Opinion dated May 17, 2016 issued in International Application No. PCT/JP2016/059971.
Yasuyuki Matsushita, et al., "Full-Frame Video Stabilization with Motion Inpainting," IEEE Transactions on Pattern Analysis and Machine Intelligence, vol. 28, No. 7, Jul. 2006, pp. 1-14.

* cited by examiner

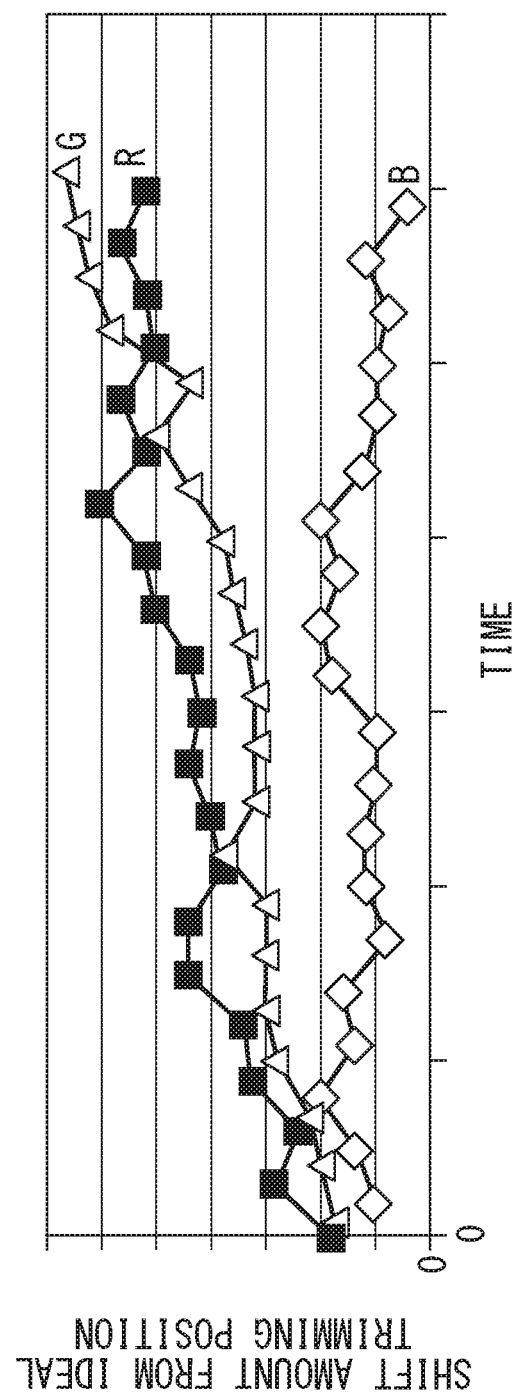

IMAGE PROCESSING DEVICE, IMAGE PROCESSING METHOD, IMAGE PROCESSING PROGRAM

CROSS-REFERENCE TO RELATED APPLICATIONS

This is a continuation of International Application PCT/JP2016/059971 which is hereby incorporated by reference herein in its entirety.

TECHNICAL FIELD

The present invention relates to an image processing device, an image processing method, and an image processing program.

BACKGROUND ART

In the related art, there is a known shake correction method for a moving image acquired by a frame sequential method (for example, see PTLs 1 and 2). In the frame sequential method, frames in a red channel, a green channel, and a blue channel (R frame, G frame, and B frame) are sequentially acquired, and the R, G, and B frames are synchronized, thereby generating a single RGB-format moving-image frame. In PTL 1, a movement amount indicating the magnitude of shake in a moving-image frame is calculated from the moving-image frame, and shake correction processing is performed on the moving-image frame on the basis of the calculated movement amount. In PTL 2, movement amounts in R, G, and B frames are respectively calculated, and shake correction processing is performed on the R, G, and B frames prior to synchronization, on the basis of the respective movement amounts.

CITATION LIST

Patent Literature

{PTL 1} Publication of Japanese Patent No. 5562808
{PTL 2} Japanese Unexamined Patent Application, Publication No. 2012-217579

SUMMARY OF INVENTION

According to a first aspect, the present invention provides a frame-sequential-type moving-image image processing device that sequentially receives frames in a plurality of color channels and that composites the frames in the plurality of color channels to generate a color moving-image frame, the image processing device including: a movement-amount calculating unit that calculates, from a latest frame and a past frame in the same color channel, a movement amount of an object image between the latest frame and the past frame; a shake-correction-amount calculating unit that calculates a shake correction amount for the latest frame on the basis of the movement amount calculated by the movement-amount calculating unit; a stable-shake-correction-amount calculating unit that calculates a stable shake-correction amount for the latest frame on the basis of the shake correction amount calculated by the shake-correction-amount calculating unit; a shake correcting unit that performs shake correction processing on the latest frame on the basis of the stable shake-correction amount calculated by the stable-shake-correction-amount calculating unit; and a storage unit that stores the stable shake-correction amount calculated by the stable-shake-correction-amount calculating unit, wherein the stable-shake-correction-amount calculating unit calculates the stable shake-correction amount for the latest frame on the basis of the shake correction amount for the latest frame and a stable shake-correction amount for a frame in a different color channel from the latest frame, stored in the storage unit.

According to a second aspect, the present invention provides a frame-sequential-type moving-image image processing method in which frames in a plurality of color channels are sequentially received, and the frames in the plurality of color channels are composited to generate a color moving-image frame, the image processing method including: a movement-amount calculation step of calculating, from a latest frame and a past frame in the same color channel, a movement amount of an object image between the latest frame and the past frame; a shake-correction-amount calculation step of calculating a shake correction amount for the latest frame on the basis of the movement amount calculated in the movement-amount calculation step; a stable-shake-correction-amount calculation step of calculating a stable shake-correction amount for the latest frame on the basis of the shake correction amount calculated in the shake-correction-amount calculation step; a shake correction step of performing shake correction processing on the latest frame on the basis of the stable shake-correction amount calculated in the stable-shake-correction-amount calculation step; and a storage step of storing the stable shake-correction amount calculated in the stable-shake-correction-amount calculation step, wherein, in the stable-shake-correction-amount calculation step, the stable shake-correction amount for the latest frame is calculated on the basis of the shake correction amount for the latest frame and a stable shake-correction amount for a frame in a different color channel from the latest frame, stored in the storage step.

According to a third aspect, the present invention provides a frame-sequential-type moving-image image processing program in which frames in a plurality of color channels are sequentially received, and the frames in the plurality of color channels are composited to generate a color moving-image frame, the image processing program causing a computer to execute: a movement-amount calculation step of calculating, from a latest frame and a past frame in the same color channel, a movement amount of an object image between the latest frame and the past frame; a shake-correction-amount calculation step of calculating a shake correction amount for the latest frame on the basis of the movement amount calculated in the movement-amount calculation step; a stable-shake-correction-amount calculation step of calculating a stable shake-correction amount for the latest frame on the basis of the shake correction amount calculated in the shake-correction-amount calculation step; a shake correction step of performing shake correction processing on the latest frame on the basis of the stable shake-correction amount calculated in the stable-shake-correction-amount calculation step; and a storage step of storing the stable shake-correction amount calculated in the stable-shake-correction-amount calculation step, wherein, in the stable-shake-correction-amount calculation step, the stable shake-correction amount for the latest frame is calculated on the basis of the shake correction amount for the latest frame and a stable shake-correction amount for a frame in a different color channel from the latest frame, stored in the storage step.

BRIEF DESCRIPTION OF DRAWINGS

FIG. 8 is a view showing example temporal changes of position-shift amounts of the trimming areas in the R, G, and B frames, when shake correction processing is performed by using the shake correction amounts.

DESCRIPTION OF EMBODIMENTS

First Embodiment

An image processing device 1 according to a first embodiment of the present invention will be described below with reference to FIGS. 1 to 11.

Figure 1:
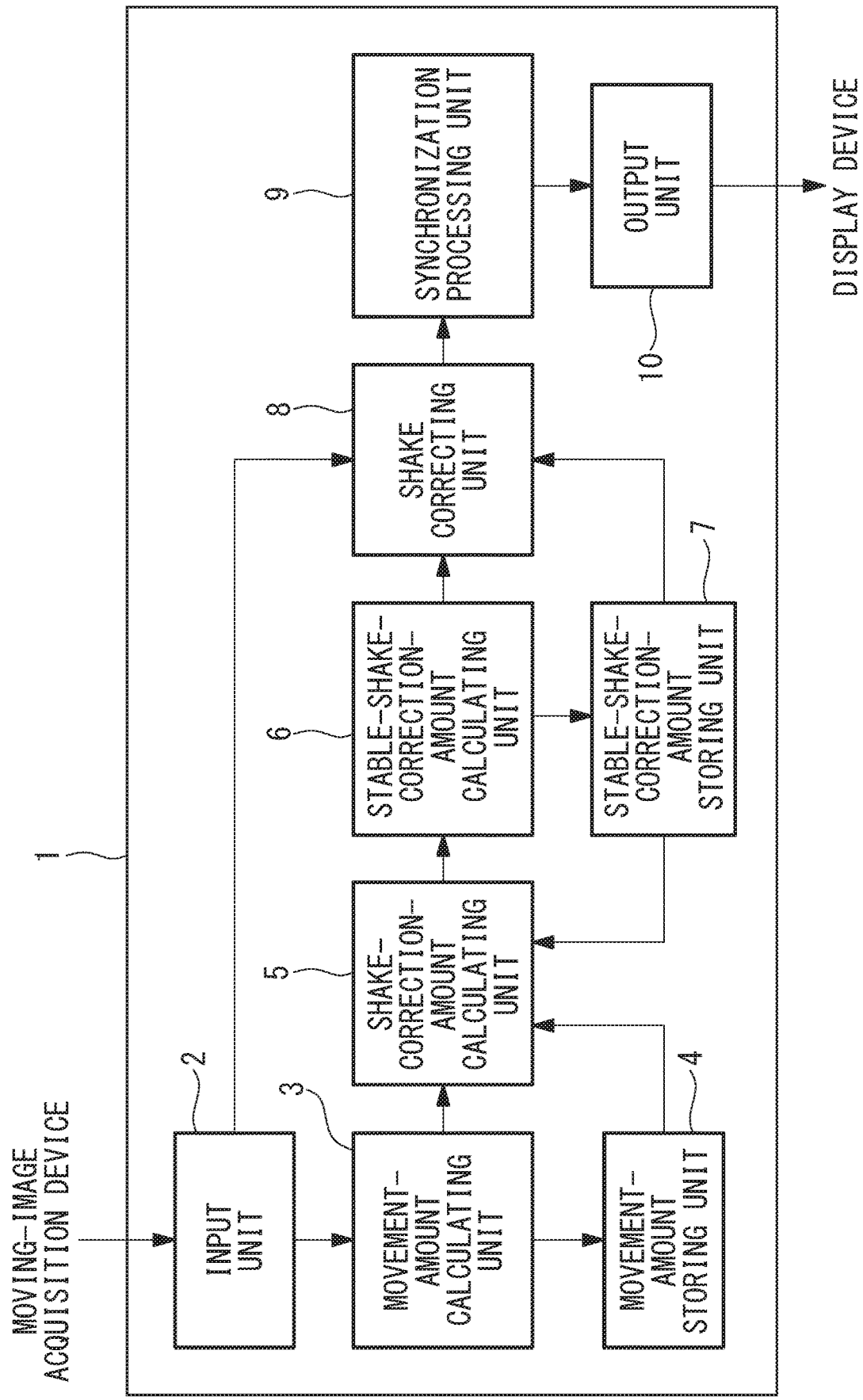
FIG. 1 is a view showing the overall configuration of an image processing device according to a first embodiment of the present invention.

As shown in FIG. 1, the image processing device 1 of this embodiment is used by being connected to a frame-sequential-type moving-image acquisition device and to a display device.

The moving-image acquisition device is, for example, an endoscopic device. Each of the moving-image frames that constitute a color moving image is composed of frames in a plurality of color channels. The frame-sequential-type moving-image acquisition device sequentially radiates a plurality of light beams in different colors onto an object and captures the object irradiated with the light beams in the respective colors, thereby sequentially acquiring frames in a plurality of color channels.

The image processing device 1 sequentially receives the frames in the plurality of color channels from the moving-image acquisition device, and subjects the frames in the plurality of color channels, which are consecutive in the time-axis direction, to synchronization processing, thereby generating a single color moving-image frame. The image processing device 1 sends the generated moving-image frame to the display device at a constant frame rate. Accordingly, a color moving image is displayed on the display device.

Figure 2:
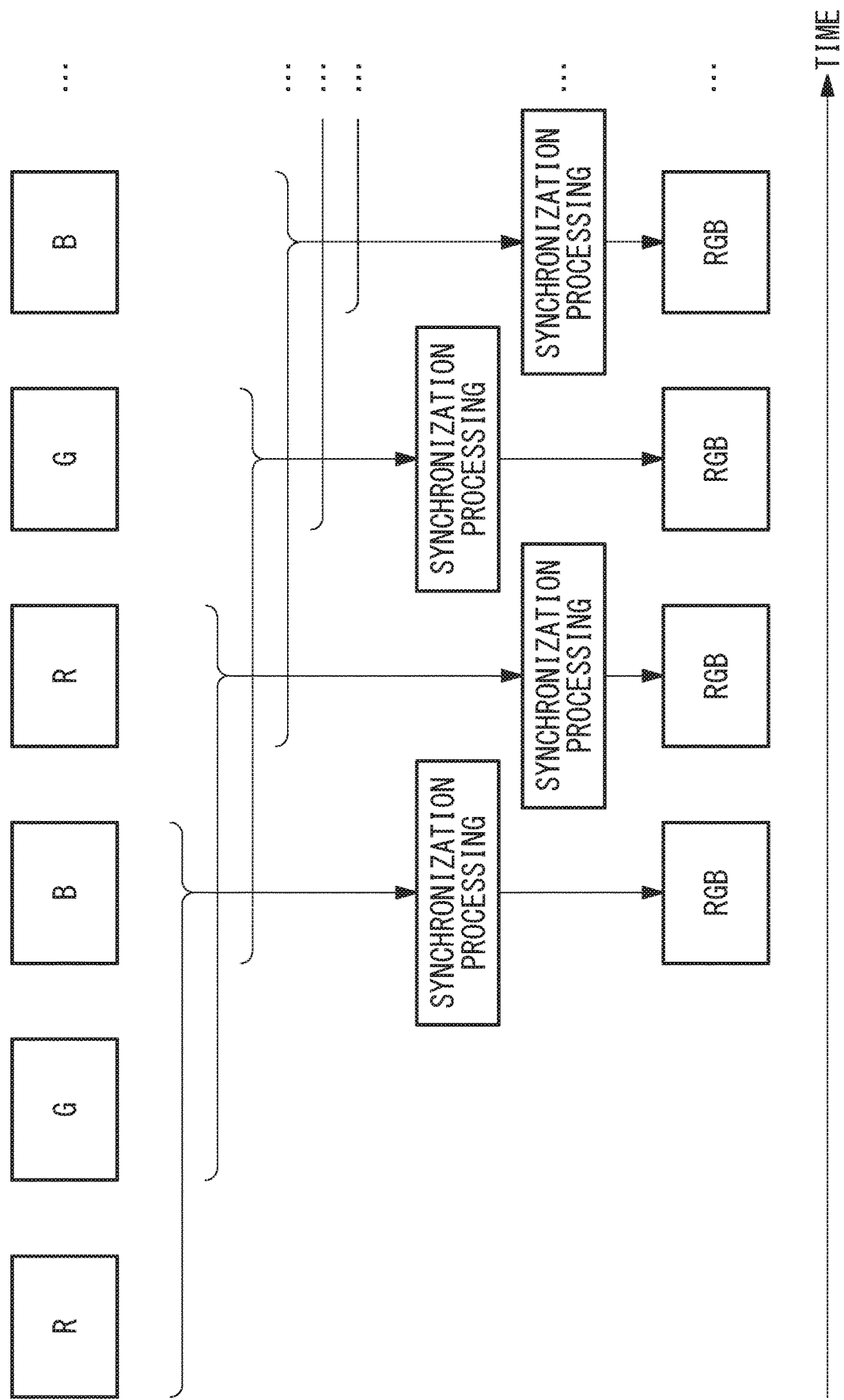
FIG. 2 is a view for explaining the relationship between frames that are input to the image processing device shown in FIG. 1 and moving-image frames that are output from the image processing device.

In this embodiment, as an example, an RGB-format moving image will be described. Therefore, the moving-image acquisition device sequentially radiates light beams in red (R), green (G), and blue (B) onto an object, sequentially and repeatedly acquires frames in R, G, and B channels (hereinafter, referred to as R frame, G frame, and B frame), and sequentially sends the acquired frames to the image processing device 1. The image processing device 1 generates a single RGB-format moving-image frame from three R, G, and B frames that are consecutive in the time-axis direction, as shown in FIG. 2.

Next, the details of the image processing device 1 will be described.

As shown in FIG. 1, the image processing device 1 is provided with: an input unit 2; a movement-amount calculating unit 3; a movement-amount storing unit 4; a shake-correction-amount calculating unit 5; a stable-shake-correction-amount calculating unit 6; a stable-shake-correction-amount storing unit 7; a shake correcting unit 8; a synchronization processing unit 9; and an output unit 10. The input unit 2 receives R, G, and B frames from the moving-image acquisition device. The movement-amount calculating unit 3 calculates movement amounts of an object image A in each of the R, G, and B frames. The movement-amount storing unit 4 stores the calculated movement amounts at least for a certain period of time. The shake-correction-amount calculating unit 5 calculates shake correction amounts for each of the R, G, and B frames on the basis of the movement amounts. The stable-shake-correction-amount calculating unit 6 calculates stable shake-correction amounts for each of the R, G, and B frames on the basis of the shake correction amounts. The stable-shake-correction-amount storing unit 7 stores the stable shake-correction amounts at least for a certain period of time. The shake correcting unit 8 applies shake correction processing to each of the R, G, and B frames on the basis of the stable shake-correction amounts. The synchronization processing unit 9 applies synchronization processing to the R, G, and B frames to which the shake correction processing has been applied, thus generating an RGB-format moving-image frame. The output unit 10 outputs the moving-image frame to the display device.

The input unit 2 sequentially and repeatedly receives an R frame, a G frame, and a B frame from the moving-image acquisition device. The input unit 2 sequentially sends the received latest frame to the movement-amount calculating unit 3 and the shake correcting unit 8.

Figure 3:
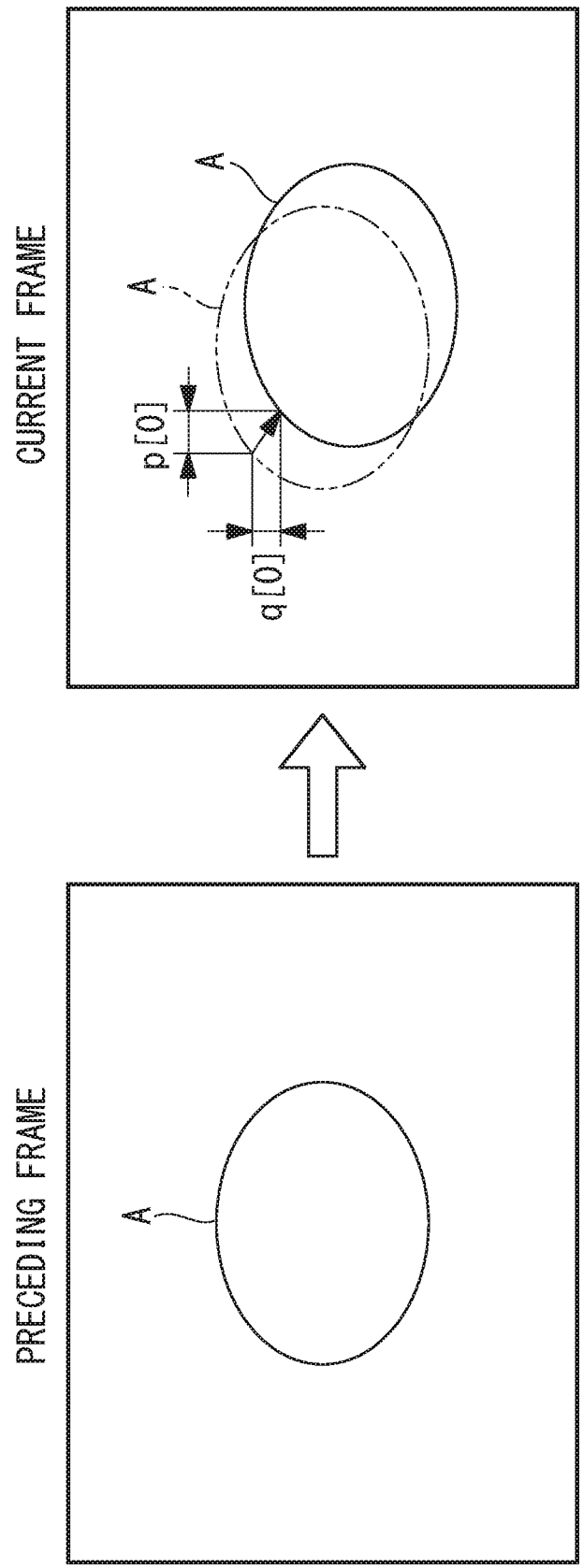
FIG. 3 is a view for explaining movement amounts calculated by a movement-amount calculating unit.

The movement-amount calculating unit 3 holds the frame received from the input unit 2 for a certain period of time. When receiving a new frame, the movement-amount calculating unit 3 calculates movement amounts p[0] and q[0] of the object image A in the latest frame (hereinafter, referred to as "current frame"). Specifically, the movement-amount calculating unit 3 compares the current frame with a preceding frame in the same color channel as the current frame (i.e., the frame three frames before the current frame, hereinafter referred to as "preceding frame") and, as shown in FIG. 3, calculates movement amounts p[0] and q[0] of the object image A in the current frame from the preceding frame. Here, p[0] and q[0] are movement amounts in the current frame in the horizontal direction (traverse direction) and the vertical direction (longitudinal direction), respectively.

The movement-amount calculating unit 3 sends the calculated movement amounts p[0] and q[0] to the movement-amount storing unit 4 and the shake-correction-amount calculating unit 5. The movement-amount storing unit 4 stores a predetermined number of latest movement amounts p[t] and q[t] (t=1, 2, ... ). Here, p[t] and q[t] are movement amounts of the object image A in the frame t-frames before the current frame.

The movement amounts p[0] and q[0] are calculated such that the current frame is divided into a plurality of block areas each having a predetermined size, a local motion vector of each of the block areas with respect to the preceding frame is calculated, and the local motion vectors of all the block areas are subjected to weighted averaging.

Known template matching processing is used to calculate a local motion vector. Specifically, the preceding frame is divided into a plurality of block areas, as in the current frame. Next, for each of the block areas of the current frame, a correlation value with each of the block areas of the preceding frame is calculated, the corresponding block area in the preceding frame is identified on the basis of the correlation value, and the difference in position with respect to the corresponding block area is calculated as the local motion vector. For example, a value based on SAD (Sum of Absolute Difference), SSD (Sum of Square Difference), or NCC (Normalized Cross Correlation) of frame brightness values is used as the correlation value used in the template matching processing.

The local-motion-vector calculation method is not limited to the above-described template matching, and another known method may be used. For example, it is also possible to use a gradient method based on a brightness gradient in the frame or a matching technique using a brightness edge in the frame as a feature point.

Instead of using unprocessed frames received from the input unit 2, the movement-amount calculating unit 3 may use frames to which various image filters, such as an edge enhancement filter and a low-pass filter, have been applied, to calculate the movement amounts.

Here, when a moving object is captured, the movement amounts of the object image A between the current frame and the preceding frame include movement amounts caused by movement of the object and movement amounts (shake amounts) caused by shaking of the moving-image acquisition device. The movement-amount calculating unit 3 decomposes the movement amounts of the object image A between the current frame and the preceding frame into the movement amounts caused by movement of the object and the shake amounts and calculates the shake amounts as the final movement amounts p[0] and q[0].

The movement amounts caused by movement of the object change slowly compared with the shake amounts. Therefore, for example, the time average of the movement amounts of the object image A between the current frame and the preceding frame is calculated as the movement amounts caused by movement of the object. The differences between: the movement amounts of the object image A between the current frame and the preceding frame; and the movement amounts caused by movement of the object are calculated as the shake amounts.

When receiving the movement amounts p[0] and q[0] in the current frame from the movement-amount calculating unit 3, the shake-correction-amount calculating unit 5 reads, from the movement-amount storing unit 4, movement amounts p[t] and q[t] (t=1, 2, ... , N) in the frames 1-N frames before the current frame and reads, from the stable-shake-correction-amount storing unit 7, stable shake-correction amounts $U_{old}$ and $V_{old}$ for a preceding frame (preceding frame) in the same color channel as the current frame. Next, from the following Expressions (1.1) and (1.2), the shake-correction-amount calculating unit 5 calculates shake correction amounts $u_{new}$ and $v_{new}$ for the current frame on the basis of the movement amounts p[0] and q[0], the movement amounts p[t] and q[t], and the stable shake-correction amounts $U_{old}$ and $V_{old}$. The shake-correction-amount calculating unit 5 sends the calculated shake correction amounts $u_{new}$ and $v_{new}$ to the stable-shake-correction-amount calculating unit 6.

$$u_{new} = U_{old} + p[0] - p_{ave} \qquad (1.1)$$

$$v_{new} = V_{old} + q[0] - q_{ave} \qquad (1.2)$$

$$\text{where } p_{ave} = \sum_{t}^{N} p[t], q_{ave} = \sum_{t}^{N} q[t]$$

In Expressions (1.1) and (1.2), $u_{new}$ and $v_{new}$ respectively indicate shake correction amounts for the current frame in the horizontal direction and the vertical direction, and $U_{old}$ and $V_{old}$ respectively indicate stable shake-correction amounts for the preceding frame in the horizontal direction and the vertical direction. $p_{ave}$ and $q_{ave}$ respectively indicate cumulative-average movement amounts in the horizontal direction and the vertical direction that are calculated by applying integral addition to the movement amounts p[t] and q[t] in the frames t (t=1, 2, ... , N) frames before the current frame. N is the number of frames to which integral addition is applied. In shake correction processing for moving-image frames, shake correction processing is consecutively performed in the time direction from the start of the shake correction processing. Expressions (1.1) and (1.2) express that correction amounts for correcting shaking of the object image A in the current frame are accumulated to the stable shake-correction amounts $U_{old}$ and $V_{old}$ for the preceding frame.

When receiving the shake correction amounts $u_{new}$ and $v_{new}$ from the shake-correction-amount calculating unit 5, the stable-shake-correction-amount calculating unit 6 reads, from the stable-shake-correction-amount storing unit 7, stable shake-correction amounts U[t] and V[t] for the preceding frames in color channels other than the color channel of the current frame. Next, the stable-shake-correction-amount calculating unit 6 performs weighted combining of the shake correction amounts $u_{new}$ and $v_{new}$ and the stable shake-correction amounts U[t] and V[t], thereby calculating the stable shake-correction amounts U[0] and V[0] for the current frame. Specifically, as shown in the following Expressions (2.1) and (2.2), the stable-shake-correction-amount calculating unit 6 multiplies the shake correction amounts $u_{new}$ and $v_{new}$ by a weight coefficient w[0], multiplies the stable shake-correction amounts U[t] and V[t] by a weight coefficient w[t], and adds the obtained products.

$$U[0] = w[0] \times u_{new} + \sum_{t}^{C-1} w[t] \times U[t] \qquad (2.1)$$

$$V[0] = w[0] \times v_{new} + \sum_{t}^{C-1} w[t] \times V[t] \quad (2.2)$$

$$\text{where } \sum_{t=0}^{C-1} w[t] = 1$$

In Expressions (2.1) and (2.2), U[t] and V[t] respectively indicate stable shake-correction amounts, in the horizontal direction and the vertical direction, for the frame t (t=1, 2, ..., C) frames before the current frame. C−1 is the number of stable shake-correction amounts used for weighted combining. In this example, although C is set on the assumption of the number of color channels (i.e., 3), C may be another number. w[0] and w[t] are weight coefficients, and the number of elements of the weight coefficients is equal to C.

The first items in the right sides of Expressions (2.1) and (2.2) indicate the degree of shake correction with respect to the current frame. As w[0] increases, shaking of the object image A in the current frame is precisely corrected. On the other hand, the second items in the right sides of Expressions (2.1) and (2.2) have an effect of bringing the shake correction amounts among the color channels close to each other. As w[t] increases, the differences in the shake correction amounts among the R, G, and B frames (the differences in the position of a trimming area) are reduced, and the effect of suppressing the occurrence of color shifts in the moving-image frame is enhanced.

The stable-shake-correction-amount calculating unit 6 sends the calculated stable shake-correction amounts U[0] and V[0] to the stable-shake-correction-amount storing unit 7 and the shake correcting unit 8.

The stable-shake-correction-amount storing unit 7 stores the stable shake-correction amounts U[t] and V[t] for a predetermined number of latest frames.

Figure 4:
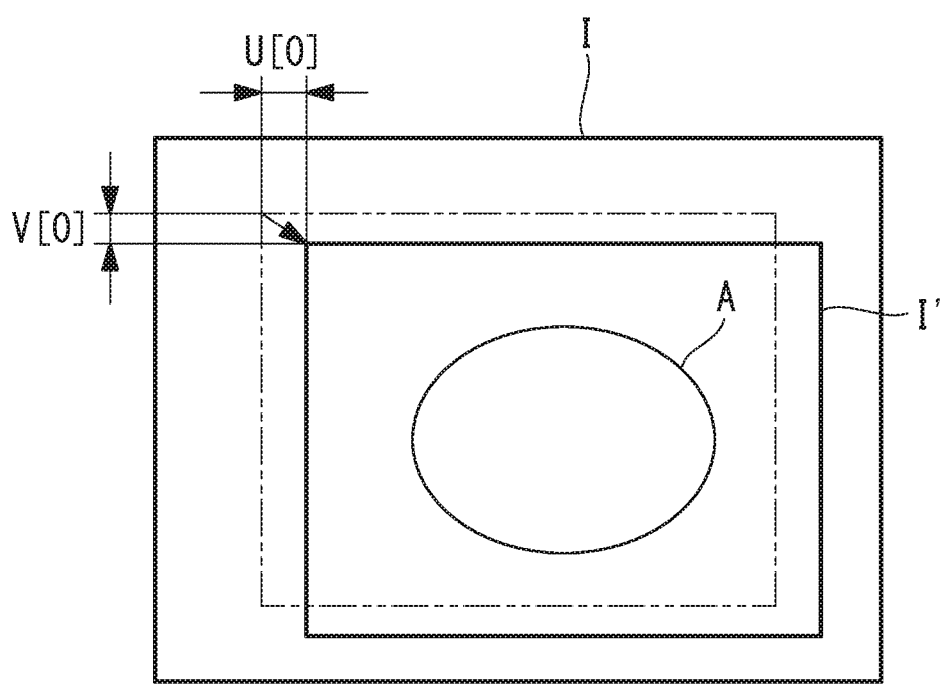
FIG. 4 is a view for explaining shake correction processing performed by a shake correcting unit.

When receiving the stable shake-correction amounts U[0] and V[0] from the stable-shake-correction-amount calculating unit 6, the shake correcting unit 8 performs shake correction processing on the current frame on the basis of the stable shake-correction amounts U[0] and V[0]. The shake correction processing is electronic camera-shake correction processing performed by adjusting the position of a trimming area. A known desired method is used for the electronic camera-shake correction processing. For example, as shown in FIG. 4, the shake correcting unit 8 sets a trimming area I' in a current frame I, moves the trimming area I' from the reference trimming-area position (for example, the position of the trimming area at the start of shake correction) by the stable shake-correction amounts U[0] and V[0] in the horizontal direction and the vertical direction, and cuts out the moved trimming area I' from the current frame I. The shake correcting unit 8 sends the cut-out trimming area I' to the synchronization processing unit 9 as a shake-corrected frame.

The shake-corrected frame I'[c](x,y) is expressed by the following Expression (3) by using the current frame I[c](x, y). In Expression (3), x is the coordinate in the horizontal direction, y is the coordinate in the vertical direction, and c (=R, G, B) is the color channel of the current frame. I[c](x,y) and I'[c](x,y) respectively indicate brightness values of a pixel at the coordinates (x,y).

$$I'[c](x,y)=I[c](x+U[0],y+V[0]) \quad (3)$$

In the above-described shake correction processing, the trimming area is moved in frames. In Expression (3), the shake correction amounts are expressed as the amounts obtained by accumulating the movement amounts of the trimming area in all frames from the frame at the start of shake correction to the current frame.

The synchronization processing unit 9 temporarily holds the shake-corrected frame received from the shake correcting unit 8. The synchronization processing unit 9 composites three shake-corrected frames generated from R, G, and B frames that are consecutive in the time-axis direction, thus generating an RGB-format moving-image frame, and sends the generated moving-image frame to the output unit 10.

The output unit 10 sends the moving-image frames to the display device at certain time intervals. Accordingly, an RGB-format moving image at a certain frame rate is displayed on the display device.

Next, the operation of the thus-configured image processing device 1 will be described.

Figure 5:
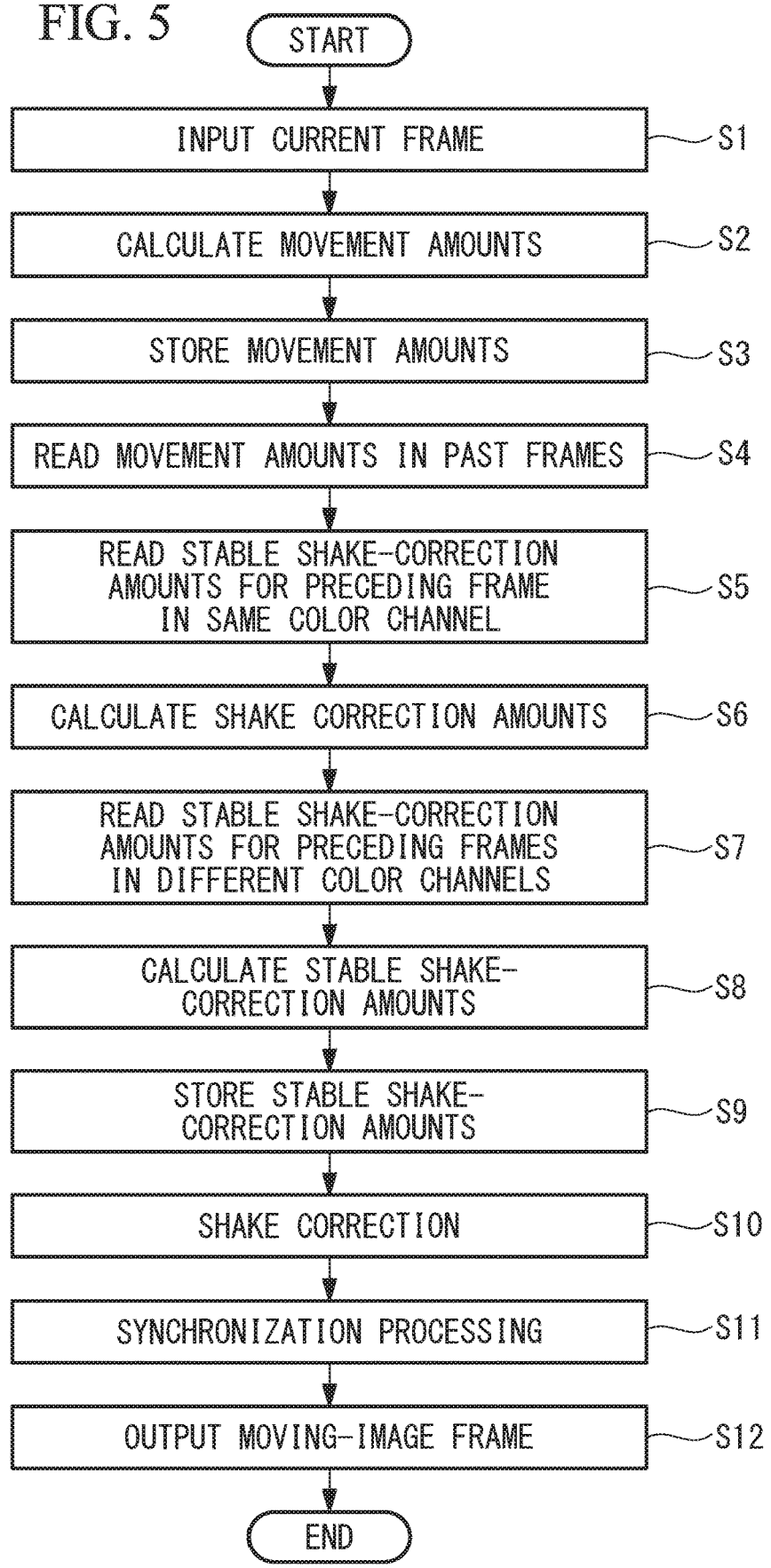
FIG. 5 is a flowchart showing an image processing method used by the image processing device shown in FIG. 1.

According to the image processing device 1 of this embodiment, as shown in FIG. 5, an R frame, a G frame, and a B frame are sequentially and repeatedly received from the moving-image acquisition device (Step S1). When the current frame is received, the movement amounts p[0] and q[0] of the object image A in the current frame from the preceding frame are calculated (movement-amount calculation step S2).

The calculated movement amounts p[0] and q[0] in the current frame are stored in the movement-amount storing unit 4 (Step S3) and are used to calculate shake correction amounts for a frame to be input thereafter to the image processing device 1.

Next, the shake correction amounts $u_{new}$ and $v_{new}$ for the current frame are calculated on the basis of the movement amounts p[0] and q[0] calculated in Step S2 (shake-correction-amount calculation step S6). At this time, the movement amounts p[t] and q[t] in several preceding frames are read from the movement-amount storing unit 4 (Step S4). The stable shake-correction amounts $U_{old}$ and $V_{old}$, which are already calculated for the preceding frame in the same color channel as the current frame and are stored, are read from the stable-shake-correction-amount storing unit 7 (Step S5). Then, the shake correction amounts $u_{new}$ and $v_{new}$ are calculated on the basis of, in addition to the movement amounts p[0] and q[0] in the current frame, the movement amounts p[t] and q[t] and the stable shake-correction amounts $U_{old}$ and $V_{old}$ read in Steps S4 and S5 (Step S6).

Next, the stable shake-correction amounts U[0] and V[0] for the current frame are calculated on the basis of the shake correction amounts $u_{new}$ and $v_{new}$ calculated in Step S6 (stable-shake-correction-amount calculation step S8). At this time, the stable shake-correction amounts U[t] and V[t], which are already calculated for the preceding frames in different color channels from the current frame and are stored, are read from the stable-shake-correction-amount storing unit 7 (Step S7). Then, the stable shake-correction amounts U[0] and V[0] are calculated on the basis of, in addition to the shake correction amounts (u, v), the stable shake-correction amounts U[t] and V[t] read in Step S7 (Step S8).

The calculated stable shake-correction amounts U[0] and V[0] for the current frame are stored in the stable-shake-correction-amount storing unit 7 (storage step S9) and are used to calculate the shake correction amounts and the stable shake-correction amounts for a frame to be input thereafter to the image processing device 1.

Next, shake correction processing is performed on the current frame on the basis of the stable shake-correction amounts U[0] and V[0] calculated in Step S8 (shake correction step S10). Next, a shake-corrected frame generated in Step S10 and two shake-corrected frames generated immediately before the shake-corrected frame are subjected to synchronization processing, thereby generating a moving-image frame (Step S11). The generated moving-image frame is output to the display device (Step S12).

Note that, while a required number of movement amounts p[t] and q[t] are accumulated in the movement-amount storing unit 4, the shake-correction-amount calculating unit 5 uses, instead of the movement amounts p[t] and q[t] in the past frames, initially-set values or the movement amounts p[0] and q[0] in the current frame. Similarly, while a required number of stable shake-correction amounts U[t] and V[t] are accumulated in the stable-shake-correction-amount storing unit 7, the shake-correction-amount calculating unit 5 and the stable-shake-correction-amount calculating unit 6 use, instead of the stable shake-correction amounts $U_{old}$ and $V_{old}$ or U[t] and V[t] for the past frames, initially-set values or shake correction amounts.

Here, the movement amounts p[0] and q[0] are calculated from two frames in the same color channel. This is because there are differences in the object image A among R, G, and B frames acquired by the frame-sequential-type moving-image acquisition device. For example, the image of a red-color object is clear in G and B frames but is unclear in an R frame. Therefore, in order to calculate precise movement amounts of the object image A, it is necessary to use frames in the same color channel.

Figure 6A:
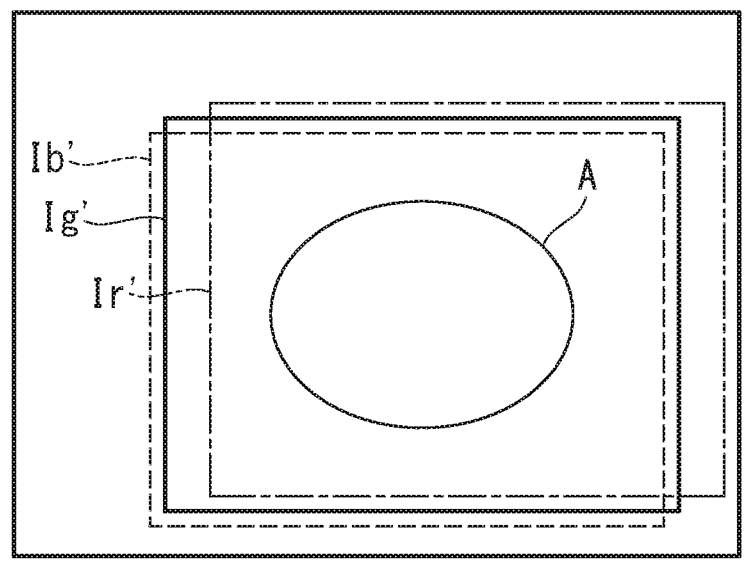
FIG. 6A is a view showing example trimming areas in R, G, and B frames when shake correction processing is performed by using shake correction amounts.
Figure 6B:
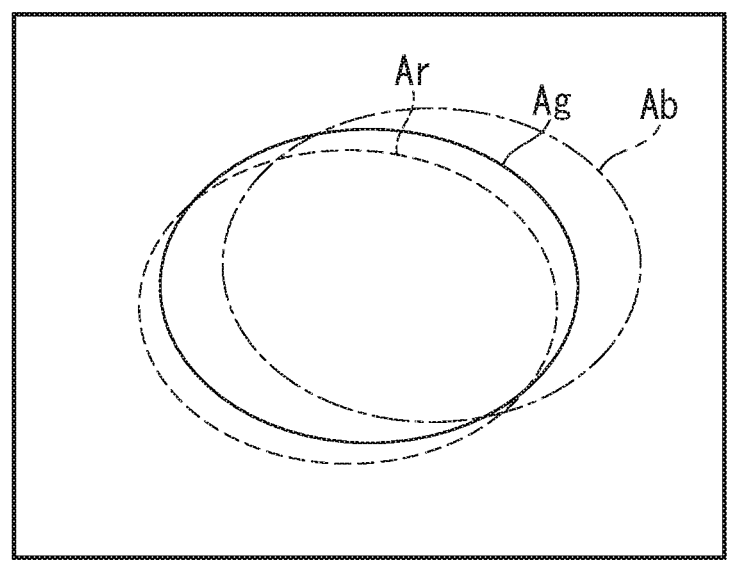
FIG. 6B is a view showing a moving-image frame generated from the trimming areas in the R, G, and B frames shown in FIG. 6A.

In this way, because the movement amounts p[0] and q[0] are calculated independently for each color channel, the movement amounts of the respective color channels cause errors independent of each other. Therefore, if shake correction processing is performed by using shake correction amounts that are based on only the movement amounts of one color channel, as shown in FIG. 6A, positional differences are caused among a trimming area Ir' in the R frame, a trimming area Ig' in the G frame, and a trimming area Ib' in the B frame. As a result, as shown in FIG. 6B, in the moving-image frame, positional differences, i.e., color shifts, are caused among an object image Ar in the R frame, an object image Ag in the G frame, and an object image Ab in the B frame.

Figure 7A:
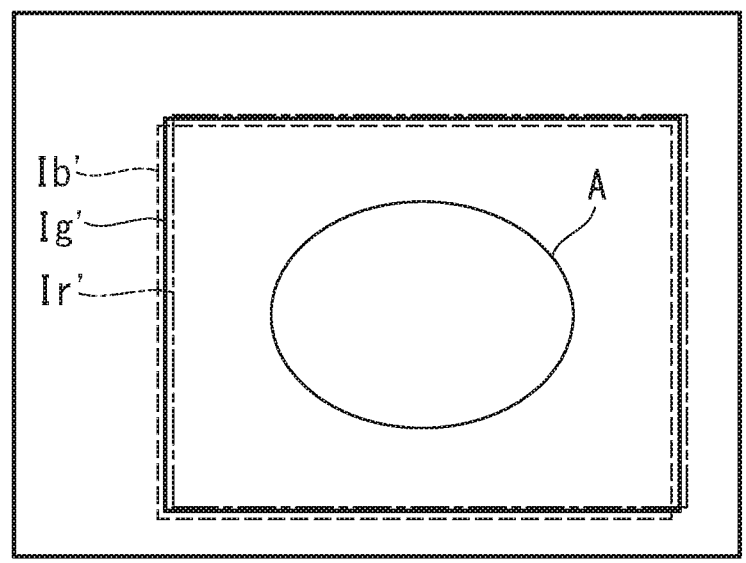
FIG. 7A is a view showing example trimming areas in R, G, and B frames when shake correction processing is performed by using stable shake-correction amounts.
Figure 7B:
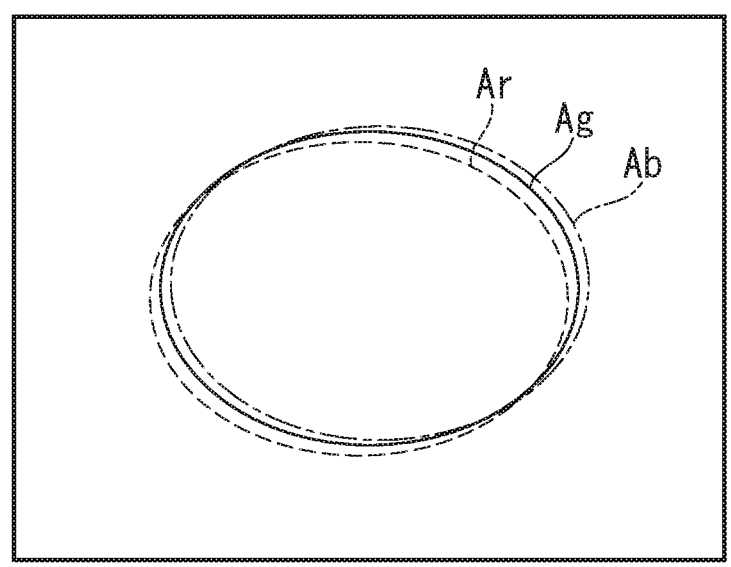
FIG. 7B is a view showing a moving-image frame generated from the trimming areas in the R, G, and B frames shown in FIG. 7A.

According to this embodiment, the stable shake-correction amounts U[0] and V[0] that depend on the stable shake-correction amounts U[t] and V[t] for frames in different color channels from the current frame are used in the shake correction processing for the current frame. In this way, the stable shake-correction amounts for the R frame, the G frame, and the B frame are made to depend on each other, thereby reducing the positional differences among the trimming areas Ir', Ig', and Ib', as shown in FIG. 7A. As a result, as shown in FIG. 7B, there is an advantage in that color shifts in the moving-image frame can be reduced.

Figure 9:
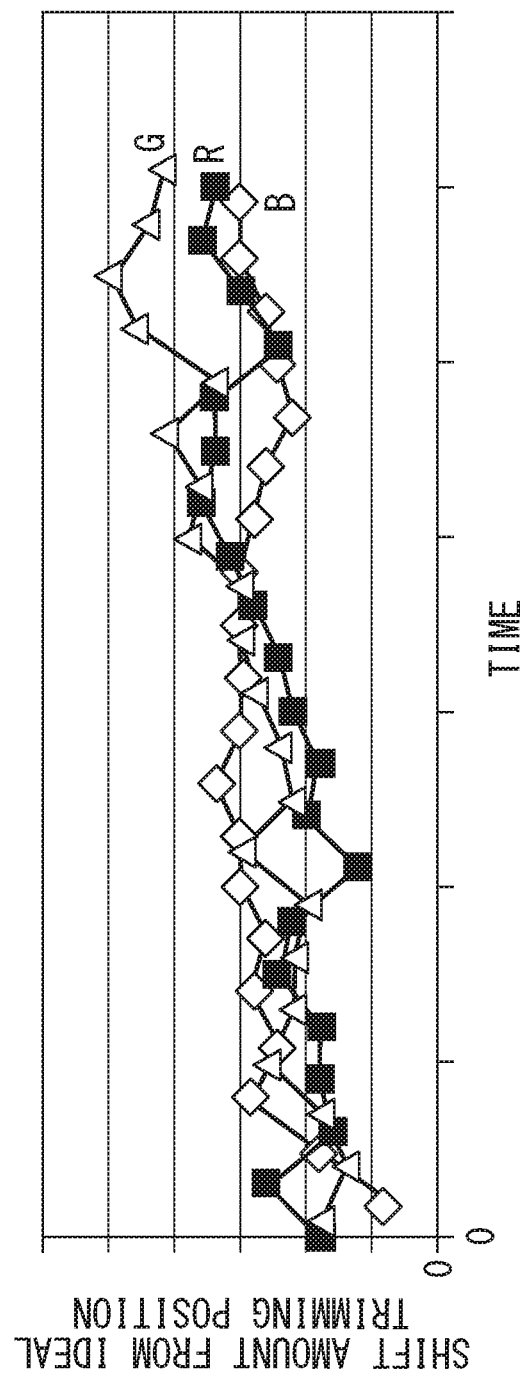
FIG. 9 is a view showing example temporal changes of position-shift amounts of the trimming areas in the R, G, and B frames, when shake correction processing is performed by using the stable shake-correction amounts.

FIGS. 8 and 9 show example temporal changes in the shift amounts of actual trimming positions in the respective R, G, and B frames with respect to an ideal trimming position, when shake correction processing is performed by using the shake correction amounts and the stable shake-correction amounts, respectively. The ideal trimming position is a trimming position when there is no error in the movement amounts calculated by the movement-amount calculating unit 3. In FIGS. 8 and 9, the differences in the shift amounts of the trimming positions among the R, G, and B frames at the same time mean the occurrence of color shifts in the moving-image frame.

As shown in FIG. 8, when the shake correction processing is performed by using the shake correction amounts, the differences in the shift amounts of the trimming positions among the R, G, and B frames are increased over time, and the color shifts are gradually increased in the moving-image frames. This is because errors in the calculated movement amounts are accumulated independently for the respective channels, and, as a result, the differences in the shake correction amounts among the color channels are gradually increased. In contrast to this, as shown in FIG. 9, when the shake correction processing is performed by using the stable shake-correction amounts, the shift amounts of the trimming positions among the R, G, and B frames are substantially the same, and it is found that color shifts are resolved in the moving-image frames.

Figure 10:
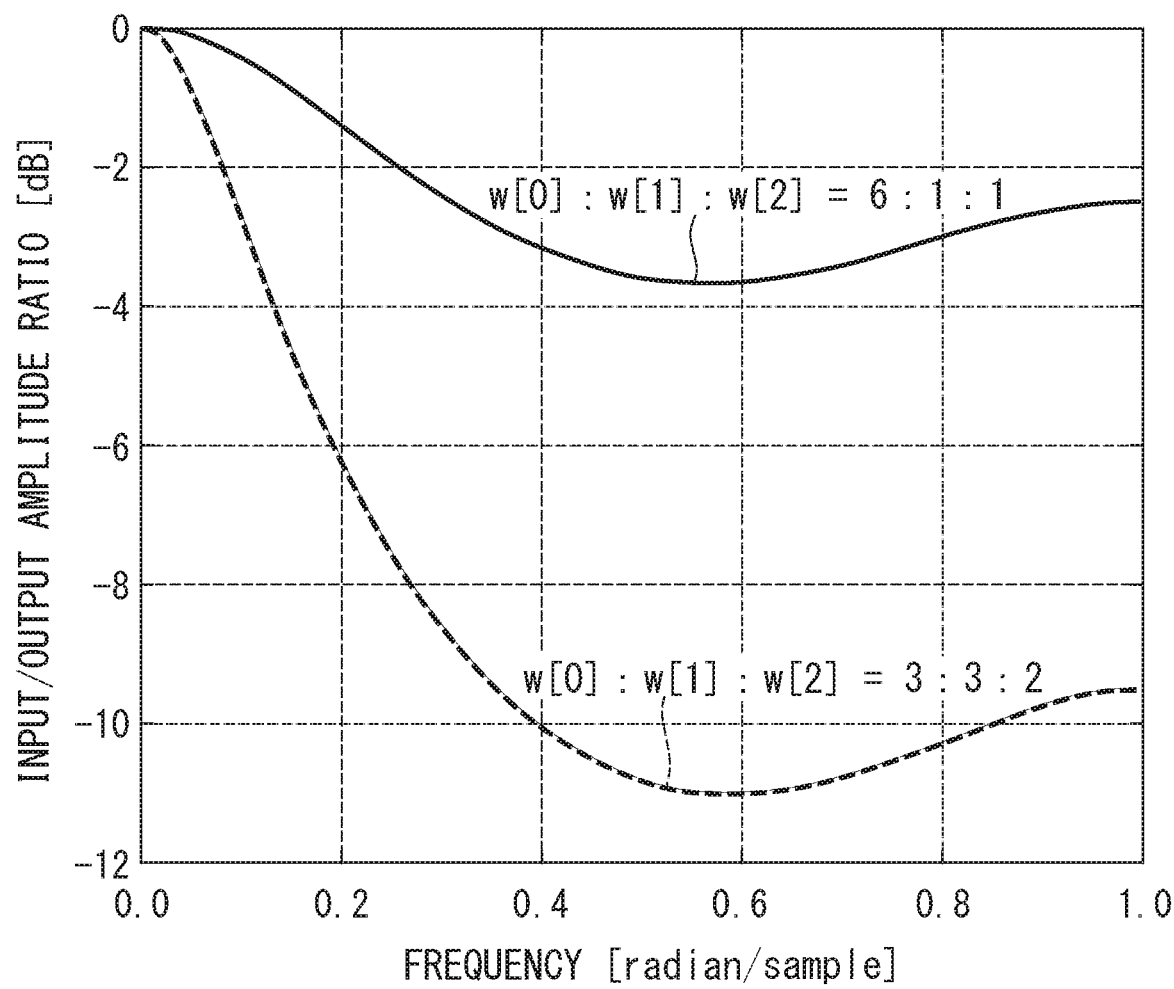
FIG. 10 is a view showing a preferable example of IIR-filter characteristics in Expressions (2.1) and (2.2).

Regarding the weight w[t] in Expressions (2.1) and (2.2), when time-series data of shake correction amounts calculated for respective frames is considered, Expressions (2.1) and (2.2) can be regarded as IIR (infinite impulse response) filters. In order to obtain a color-shift suppressing effect, the weight coefficients w[0], w[1], and w[2] with which the IIR filter has characteristics for attenuating high-frequency components may be set. FIG. 10 shows example characteristics of a preferable IIR filter. As shown in FIG. 10, when C is equal to 3, setting w[0]:w[1]:w[2] to 6:1:1 or 3:3:2 is effective in reducing color shifts.

The data shown in FIG. 10 was obtained from the following simulation experiment.

Figure 11:
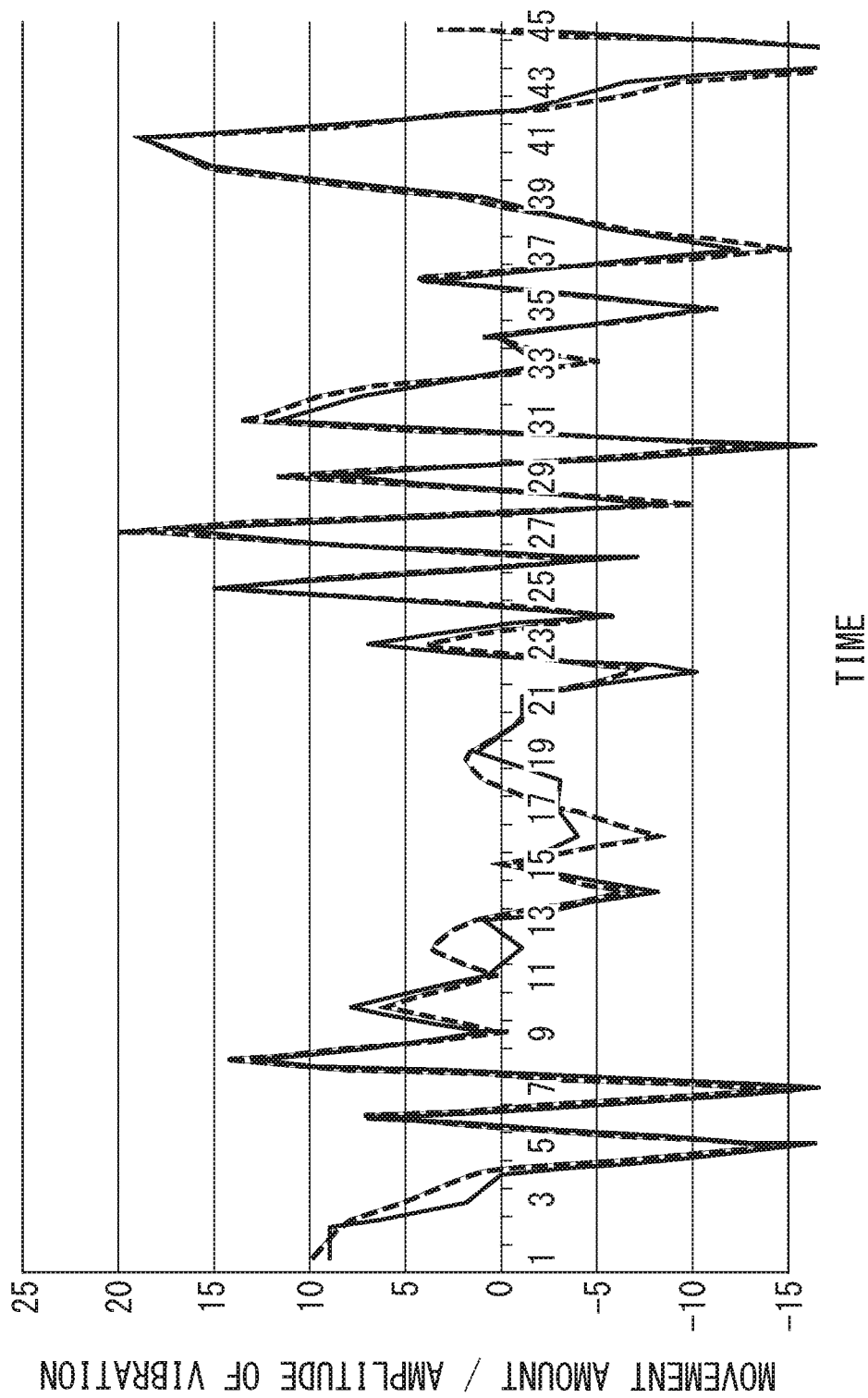
FIG. 11 is a graph showing temporal changes of a camera-shake amount and a movement amount used for the simulation shown in FIG. 10.

A scene in which a completely stationary object is captured with a hand-held video camera was simulated, and the scene, in which camera-shaking occurs as a movement amount, was set in frames. Specifically, the scene was set to a scene that vibrates on the basis of a random number generated according to a normal distribution in which the mean is zero, and the standard deviation is 6. Furthermore, the movement amount was set to include an error based on a random number generated according to a normal distribution in which the mean is zero, and the standard deviation is 2. Under such condition settings, the movement amount shown in FIG. 11 was obtained. In FIG. 11, the solid line shows vibration of the scene, and the dashed line shows the movement amount.

Second Embodiment

Next, an image processing device according to a second embodiment of the present invention will be described with reference to FIG. 12.

In the first embodiment, the stable-shake-correction-amount calculating unit 6 uses predetermined weight coefficients w[t] (t=0, 1, 2, . . . , C) to calculate the stable shake-correction amounts. In contrast to this, the image processing device of this embodiment differs from that of the first embodiment in that the movement-amount calculating unit 3 further calculates, in addition to the movement amounts p[0] and q[0], the reliability $w_{rel}$ of the movement amounts p[0] and q[0], and the stable-shake-correction-amount calculating unit 6 determines weights to be given to the shake correction amounts $u_{new}$ and $v_{new}$ and the stable shake-correction amounts U[t] and V[t], on the basis of the reliability $w_{rel}$.

Figure 12:
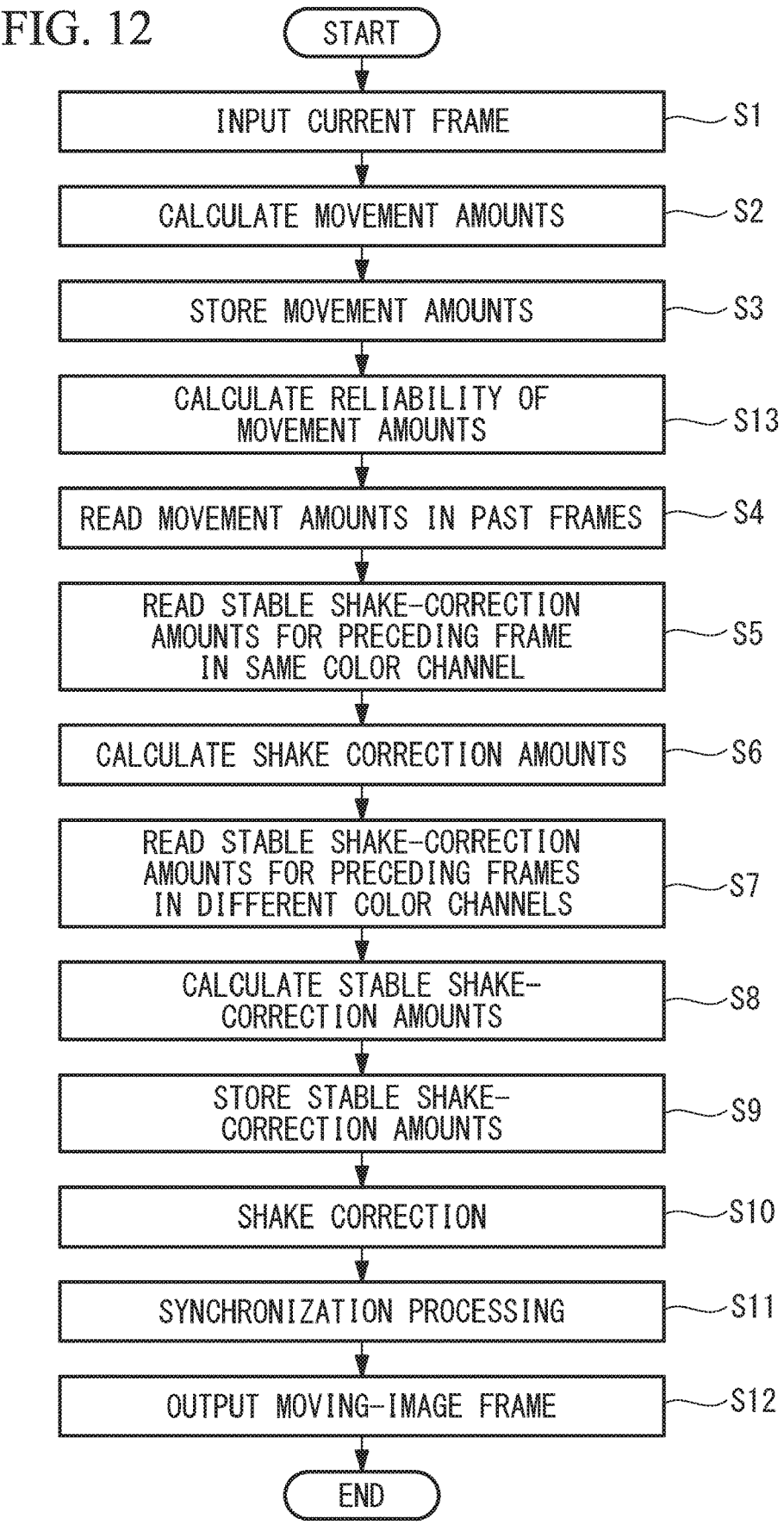
FIG. 12 is a flowchart showing an image processing method used by an image processing device according to a second embodiment of the present invention.

As shown in FIG. 12, the movement-amount calculating unit 3 calculates the movement amounts p[0] and q[0] in Step S2 and then calculates the reliability $w_{rel}$ of the movement amounts p[0] and q[0] (Step S13). In a case in which noise is contained in the R, G, and B frames, or in a case in which the R, G, and B frames contain fewer edges or textures that have brightness effective to calculate the movement amounts, the calculation accuracy of the movement amounts p[0] and q[0] could be reduced. Furthermore, in the frame sequential method, because brightness values differ among the R, G, and B frames, the calculation accuracy of the movement amounts could be different for each color channel.

The reliability $w_{rel}$ is a value expressing the calculation accuracy of the movement amounts p[0] and q[0] and has a value from 0 to 1. The value of the reliability $w_{rel}$ becomes closer to 1 as the calculation accuracy of the movement amounts p[0] and q[0] becomes higher and becomes closer to 0 as the calculation accuracy of the movement amounts p[0] and q[0] becomes lower. To calculate the reliability $w_{rel}$, for example, a method for calculating the reliability of each local motion vector and calculating, as the reliability $w_{rel}$ the ratio of the number of local motion vectors whose reliabilities are equal to or higher than a predetermined threshold is used. As the calculation method for the reliability of a local motion vector, a known desired method (for example, a method described in Japanese Unexamined Patent Application, Publication No. 2010-41416) is used.

Alternatively, in a case in which information about the calculation accuracy of the movement amounts p[0] and q[0] in a frame in each color channel exists in advance, the reliability $w_{rel}$ may be set for each color channel on the basis of the information. For example, it is effective that the reliability $w_{rel}$ for a color channel in which a useful feature of the object image A is easily detected in the template matching processing is set larger than the reliabilities for the other color channels.

In Step S8 of this embodiment, the stable-shake-correction-amount calculating unit 6 calculates the stable shake-correction amounts U[t] and V[t] on the basis of the following Expressions (4.1) and (4.2), instead of Expressions (2.1) and (2.2). Specifically, the stable-shake-correction-amount calculating unit 6 adjusts weights to be given to the shake correction amounts $u_{new}$ and $v_{new}$ and the stable shake-correction amounts U[t] and V[t] on the basis of the reliability $w_{rel}$ such that, as the reliability $w_{rel}$ of the movement amounts p[0] and q[0] increases, the weight to be given to the shake correction amounts $u_{new}$ and $v_{new}$ is increased, and the weight to be given to the stable shake-correction amounts U[t] and V[t] is reduced.

$$U[0] = w_{rel} \times w[0] \times u_{new} + (1 - w_{rel}) \sum_{t=1}^{C-1} \{w[t] \times U[t]\} \quad (4.1)$$

$$V[0] = w_{rel} \times w[0] \times v_{new} + (1 - w_{rel}) \sum_{t=1}^{C-1} \{w[t] \times V[t]\} \quad (4.2)$$

$$\text{where } \sum_{t=0}^{C-1} w[t] = 1$$

In this way, according to this embodiment, the weight coefficients used to calculate the stable shake-correction amounts U[0] and V[0] are adjusted on the basis of the reliability $w_{rel}$ of the movement amounts p[0] and q[0]. Accordingly, there is an advantage in that the influence of movement amounts p[0] and q[0] calculated with low calculation accuracy on the stable shake-correction amounts U[0] and V[0] is suppressed, thus making it possible to calculate more precise stable shake-correction amounts U[0] and V[0] and to further reduce color shifts in the moving-image frame.

In the above-described first and second embodiments, for ease of explanation and understanding, a method based on motion vectors among frames has been described as the method for calculating the movement amounts p[0] and q[0], used by the movement-amount calculating unit 3; however, the movement-amount calculation method is not limited thereto. For example, the movement amounts can be calculated by using an acceleration sensor.

In the above-described first and second embodiments, although motion vectors in the horizontal direction and the vertical direction are calculated as the movement amounts p[0] and q[0] calculated by the movement-amount calculating unit 3, instead of this, or in addition thereto, it is also possible to calculate, as the movement amounts, the magnification, rotation, and distortion of the object image A. These movement amounts can be expressed in a matrix (for example, see the document "Full-frame video stabilization with motion inpainting, PAMI2006, IEEE Transactions, Volume 28, Issue 7, pp. 1150-1163, Matsushita et al").

In the above-described first and second embodiments, although the electronic camera-shake correction processing is used as the shake correction processing, instead of this, another shake correction processing may be used. For example, optical camera-shake correction processing may be used. Specifically, the image processing device 1 of this embodiment may be combined with a moving-image acquisition device that includes a camera-shake correction lens, an image acquisition element, and a drive control unit, and the drive control unit may relatively move the camera-shake correction lens and the image acquisition element in a direction intersecting the optical axis, on the basis of the stable shake-correction amounts calculated by the stable-shake-correction-amount calculating unit 6.

The above-described image processing device 1 is formed of, for example, a dedicated or general-purpose processor. Specifically, the processor is provided with a central processing unit (CPU), a main storage device, such as RAM, and an auxiliary storage device. The auxiliary storage device is a computer-readable non-transitory storage medium, such as an HDD or various types of memory, and stores an image processing program for causing the CPU to execute processing (Steps S2 to S13) performed by the above-described respective units 3, 5, 6, 8, and 9. The image processing program is read from the auxiliary storage device to the main storage device and is executed, thereby realizing the above-described image processing.

Alternatively, the respective units 3, 5, 6, 8, and 9 of the image processing device 1 may be realized by a dedicated circuit for performing the functions of the units 3, 5, 6, 8, and 9.

The above-described embodiment leads to the following invention.

According to a first aspect, the present invention provides a frame-sequential-type moving-image image processing device that sequentially receives frames in a plurality of color channels and that composites the frames in the plurality of color channels to generate a color moving-image frame, the image processing device including: a movement-amount calculating unit that calculates, from a latest frame and a past frame in the same color channel, a movement amount of an object image between the latest frame and the past frame; a shake-correction-amount calculating unit that calculates a shake correction amount for the latest frame on the basis of the movement amount calculated by the movement-amount calculating unit; a stable-shake-correction-amount calculating unit that calculates a stable shake-correction amount for the latest frame on the basis of the shake correction amount calculated by the shake-correction-amount calculating unit; a shake correcting unit that performs shake correction processing on the latest frame on the basis of the stable shake-correction amount calculated by the stable-shake-correction-amount calculating unit; and a storage unit that stores the stable shake-correction amount calculated by the stable-shake-correction-amount calculating unit, wherein the stable-shake-correction-amount calculating unit calculates the stable shake-correction amount for the latest frame on the basis of the shake correction amount for the latest frame and a stable shake-correction amount for a frame in a different color channel from the latest frame, stored in the storage unit.

According to this aspect, when the latest frame is received, the movement-amount calculating unit calculates a movement amount of an object from the latest frame and a past frame in the same color channel, and the shake-correction-amount calculating unit calculates a shake correction amount for the latest frame on the basis of the movement amount. Furthermore, the stable-shake-correction-amount calculating unit calculates a stable shake-correction amount for the latest frame on the basis of the shake correction amount, the stable shake-correction amount is stored in the storage unit, and the shake correcting unit performs shake correction processing on the latest frame on the basis of the stable shake-correction amount. Therefore, the frames in the plurality of color channels that have been subjected to the shake correction processing are composited, thereby making it possible to generate a color moving-image frame in which shake has been corrected.

In this case, the stable shake-correction amount is calculated on the basis of not only the shake correction amount for the latest frame but also the stable shake-correction amount for a past frame in a different color channel from the latest frame. In this way, the stable shake-correction amounts for the frames in the plurality of color channels are made to depend on each other, thereby reducing, in the stable shake-correction amounts, errors among the color channels caused in the shake correction amounts. Therefore, the stable shake-correction amounts are used in shake correction processing performed on frames in the respective color channels, thereby making it possible to reduce color shifts in the moving-image frame.

In the above-described first aspect, the stable-shake-correction-amount calculating unit may weight each of the shake correction amount for the latest frame and the stable shake-correction amount for the frame in the different color channel from the latest frame and may add the weighted shake correction amount and the weighted stable shake-correction amount, thus calculating the stable shake-correction amount for the latest frame.

By doing so, it is possible to easily adjust, by using weights, the degrees of contribution of the shake correction amount for the latest frame and of the stable shake-correction amount for a frame in a different color channel from the latest frame, in the stable shake-correction amount for the latest frame.

In the above-described first aspect, the movement-amount calculating unit may further calculate the reliability of the movement amount; and the stable-shake-correction-amount calculating unit may determine a weight to be given to each of the shake correction amount for the latest frame and the stable shake-correction amount for the frame in the different color channel from the latest frame, on the basis of a reliability of the movement amount calculated from the latest frame.

By doing so, it is possible to calculate the stable shake-correction amount for which the influence of the movement amount calculated with low calculation accuracy is suppressed.

In the above-described first aspect, the plurality of color channels may be a red channel, a green channel, and a blue channel.

By doing so, it is possible to generate an RGB-format moving-image frame.

According to a second aspect, the present invention provides a frame-sequential-type moving-image image processing method in which frames in a plurality of color channels are sequentially received, and the frames in the plurality of color channels are composited to generate a color moving-image frame, the image processing method including: a movement-amount calculation step of calculating, from a latest frame and a past frame in the same color channel, a movement amount of an object image between the latest frame and the past frame; a shake-correction-amount calculation step of calculating a shake correction amount for the latest frame on the basis of the movement amount calculated in the movement-amount calculation step; a stable-shake-correction-amount calculation step of calculating a stable shake-correction amount for the latest frame on the basis of the shake correction amount calculated in the shake-correction-amount calculation step; a shake correction step of performing shake correction processing on the latest frame on the basis of the stable shake-correction amount calculated in the stable-shake-correction-amount calculation step; and a storage step of storing the stable shake-correction amount calculated in the stable-shake-correction-amount calculation step, wherein, in the stable-shake-correction-amount calculation step, the stable shake-correction amount for the latest frame is calculated on the basis of the shake correction amount for the latest frame and a stable shake-correction amount for a frame in a different color channel from the latest frame, stored in the storage step.

According to a third aspect, the present invention provides a frame-sequential-type moving-image image processing program in which frames in a plurality of color channels are sequentially received, and the frames in the plurality of color channels are composited to generate a color moving-image frame, the image processing program causing a computer to execute: a movement-amount calculation step of calculating, from a latest frame and a past frame in the same color channel, a movement amount of an object image between the latest frame and the past frame; a shake-correction-amount calculation step of calculating a shake correction amount for the latest frame on the basis of the movement amount calculated in the movement-amount calculation step; a stable-shake-correction-amount calculation step of calculating a stable shake-correction amount for the latest frame on the basis of the shake correction amount calculated in the shake-correction-amount calculation step; a shake correction step of performing shake correction processing on the latest frame on the basis of the stable shake-correction amount calculated in the stable-shake-correction-amount calculation step; and a storage step of storing the stable shake-correction amount calculated in the stable-shake-correction-amount calculation step, wherein, in the stable-shake-correction-amount calculation step, the stable shake-correction amount for the latest frame is calculated on the basis of the shake correction amount for the latest frame and a stable shake-correction amount for a frame in a different color channel from the latest frame, stored in the storage step.

REFERENCE SIGNS LIST 1 image processing device
2 input unit
3 movement-amount calculating unit
4 movement-amount storing unit
5 shake-correction-amount calculating unit
6 stable-shake-correction-amount calculating unit
7 stable-shake-correction-amount storing unit (storage unit)
8 shake correcting unit
9 synchronization processing unit
10 output unit
S2 movement-amount calculation step
S6 shake-correction-amount calculation step
S8 stable-shake-correction-amount calculation step
S9 storage step
S10 shake correction step

The invention claimed is:

1. A frame-sequential-type moving-image image processing device that sequentially receives frames in a plurality of color channels and that composites the frames in the plurality of color channels to generate a color moving-image frame, the image processing device comprising:
a computer that is configured to:
calculate, from a latest frame and a past frame in the same color channel, a movement amount of an object image between the latest frame and the past frame;
calculate a shake correction amount for the latest frame on the basis of the calculated movement amount;
calculate a stable shake-correction amount for the latest frame on the basis of the calculated shake correction amount;
perform shake correction processing on the latest frame on the basis of the calculated stable shake-correction amount; and
store the calculated stable shake-correction amount,
wherein the computer is configured to calculate the stable shake-correction amount for the latest frame on the basis of the shake correction amount for the latest frame and a stored stable shake-correction amount for a frame in a different color channel from the latest frame.

2. An image processing device according to claim 1, wherein the computer is configured to weight each of the shake correction amount for the latest frame and the stable shake-correction amount for the frame in the different color channel from the latest frame and to add the weighted shake correction amount and the weighted stable shake-correction amount, thus calculating the stable shake-correction amount for the latest frame.

3. An image processing device according to claim 2, wherein the computer is configured to:
further calculate a reliability of the movement amount in the latest frame; and
determine a weight to be given to each of the shake correction amount for the latest frame and the stable shake-correction amount for the frame in the different color channel from the latest frame, on the basis of the calculated reliability of the movement amount.

4. An image processing device according to claim 1, wherein the plurality of color channels are a red channel, a green channel, and a blue channel.

5. A frame-sequential-type moving-image image processing method in which frames in a plurality of color channels are sequentially received, and the frames in the plurality of color channels are composited to generate a color moving-image frame, the image processing method comprising:
calculating, from a latest frame and a past frame in the same color channel, a movement amount of an object image between the latest frame and the past frame;
calculating a shake correction amount for the latest frame on the basis of the calculated movement amount;
calculating a stable shake-correction amount for the latest frame on the basis of the calculated shake correction amount;
performing shake correction processing on the latest frame on the basis of the calculated stable shake-correction amount; and
storing the calculated stable shake-correction amount,
wherein the stable shake-correction amount for the latest frame is calculated on the basis of the shake correction amount for the latest frame and a stored stable shake-correction amount for a frame in a different color channel from the latest frame.

6. A non-transitory computer-readable medium having a frame-sequential-type moving-image image processing program stored thereon in which frames in a plurality of color channels are sequentially received, and the frames in the plurality of color channels are composited to generate a color moving-image frame, the image processing program causing a computer to execute functions of:
calculating, from a latest frame and a past frame in the same color channel, a movement amount of an object image between the latest frame and the past frame;
calculating a shake correction amount for the latest frame on the basis of the calculated movement amount;
calculating a stable shake-correction amount for the latest frame on the basis of the calculated shake correction amount;
performing shake correction processing on the latest frame on the basis of the calculated stable shake-correction amount; and
storing the calculated stable shake-correction amount,
wherein the stable shake-correction amount for the latest frame is calculated on the basis of the shake correction amount for the latest frame and a stored stable shake-correction amount for a frame in a different color channel from the latest frame.

* * * * *